US00PP27267P2

(12) United States Plant Patent
Oliver

(10) Patent No.: US PP27,267 P2
(45) Date of Patent: Oct. 11, 2016

(54) ***PHLOX* PLANT NAMED 'DAUGHTER OF PEARL'**

(50) Latin Name: ***Phlox carolina*×*Phlox maculata***
Varietal Denomination: Daughter of Pearl

(71) Applicant: Charles G. Oliver, Scottdale, PA (US)

(72) Inventor: Charles G. Oliver, Scottdale, PA (US)

( * ) Notice: Subject to any disclaimer, the term of this patent is extended or adjusted under 35 U.S.C. 154(b) by 84 days.

(21) Appl. No.: 14/544,219

(22) Filed: Dec. 9, 2014

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — C. A. Whealy

(57) ABSTRACT

A new and distinct *Phlox* plant named 'Daughter of Pearl', characterized by its upright and mounding plant form; vigorous growth habit; freely basal branching habit; early and freely flowering habit; large conical inflorescences with white and purple-colored flowers; and resistance to Powdery Mildew.

2 Drawing Sheets

Botanical designation: *Phlox carolina*×*Phlox maculata.*
Cultivar denomination: 'DAUGHTER OF PEARL'.

BACKGROUND OF THE INVENTION

The present invention relates to a new and distinct *Phlox* plant, botanically known as *Phlox carolina*×*Phlox maculata* and hereinafter referred to by the name 'Daughter of Pearl'.

The new *Phlox* plant is a product of a planned breeding program conducted by the Inventor in Upper Tyrone Township, Pa. The objective of the breeding program is to create new vigorous *Phlox* plants with early flowering habit, attractive leaf and flower coloration and resistance to Powdery Mildew.

The new *Phlox* plant originated from a cross-pollination conducted by the Inventor in July, 2007 of *Phlox carolina* 'Minnie Pearl', not patented, as the female, or seed, parent with *Phlox maculata* 'Alpha', not patented, as the male, or pollen, parent. The new *Phlox* plant was discovered and selected by the Inventor as a single flowering plant within the progeny of the stated cross-pollination in a controlled environment in Upper Tyrone Township, Pa. in June, 2008.

Asexual reproduction of the new *Phlox* plant by vegetative stem cuttings in a controlled greenhouse environment in Upper Tyrone Township, Pa. since 2009 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Daughter of Pearl'. These characteristics in combination distinguish 'Daughter of Pearl' as a new and distinct *Phlox* plant:

1. Upright and mounding plant form.
2. Vigorous growth habit.
3. Freely basal branching habit.
4. Early and freely flowering habit.
5. Large conical inflorescences with white and purple-colored flowers.
6. Resistance to Powdery Mildew.

Plants of the new *Phlox* differ from plants of the female parent, 'Minnie Pearl', in the following characteristics:

1. Plants of the new *Phlox* are taller and denser than plants of 'Minnie Pearl'.
2. Inflorescences of plants of the new *Phlox* are conical in shape whereas inflorescences of plants of 'Minnie Pearl' are flat-topped.
3. Plants of the new *Phlox* and 'Minnie Pearl' differ in flower color as plants of 'Minnie Pearl' have white-colored flowers.

Plants of the new *Phlox* differ from plants of the male parent, 'Alpha', in the following characteristics:

1. Leaves of plants of the new *Phlox* are not as glossy as leaves of plants of 'Alpha'.
2. Inflorescences of plants of the new *Phlox* are conical in shape whereas inflorescences of plants of 'Alpha' are flat-cylindrical in shape.
3. Inflorescences of plants of the new *Phlox* are denser than inflorescences of plants of 'Alpha'.
4. Plants of the new *Phlox* and 'Alpha' differ in flower color as plants of 'Alpha' have magenta pink-colored flowers.
5. Plants of the new *Phlox* are resistant to Powdery Mildew whereas plants of 'Alpha' are susceptible to Powdery Mildew.

Plants of the new *Phlox* can be compared to plants of *Phlox maculata* 'Omega', not patented. In side-by-side comparisons, plants of the new *Phlox* and 'Omega' differed in the following characteristics:

1. Plants of the new *Phlox* were taller than plants of 'Omega'.

2. Inflorescences of plants of the new *Phlox* were conical in shape whereas inflorescences of plants of 'Omega' were cylindrical in shape.
3. Inflorescences of plants of the new *Phlox* had more flowers per inflorescence than plants of 'Omega'.
4. Plants of the new *Phlox* had slightly smaller flowers than plants of 'Omega'.
5. Plants of the new *Phlox* and 'Omega' differed in flower color as plants of 'Omega' had red purple-colored flowers.
6. Plants of the new *Phlox* had shorter peduncles than plants of 'Omega'.
7. Plants of the new *Phlox* were resistant to Powdery Mildew whereas plants of 'Omega' were susceptible to Powdery Mildew.

Plants of the new *Phlox* can also be compared to plants of *Phlox maculata* 'Flower Power', disclosed in U.S. Plant Pat. No. 17,551. In side-by-side comparisons, plants of the new *Phlox* and 'Flower Power' differed in the following characteristics:

1. Inflorescences of plants of the new *Phlox* were conical in shape whereas inflorescences of plants of 'Flower Power' were cylindrical in shape.
2. Inflorescences of plants of the new *Phlox* had more flowers per inflorescence than plants of 'Flower Power'.
3. Plants of the new *Phlox* and 'Flower Power' differed slightly in flower color.
4. Plants of the new *Phlox* were resistant to Powdery Mildew whereas plants of 'Flower Power' were susceptible to Powdery Mildew.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Daughter of Pearl'.

The photograph at the top of the sheet is a close-up view of a typical flowering plant of 'Daughter of Pearl'.

DETAILED BOTANICAL DESCRIPTION

The aforementioned photographs and following observations, measurements and values describe plants grown during the spring and summer in one-gallon containers in a polyethylene-covered greenhouse and an outdoor nursery in Upper Tyrone Township, Pa. and under cultural practices typical of *Phlox* production. During the production of the plants, day temperature averaged 26° C. and night temperatures averaged 15° C. Plants were two years old when the photographs and description were taken. In the following description, color references are made to The Royal Horticultural Society Colour Chart, 1995 Edition, except where general terms of ordinary dictionary significance are used.

Botanical classification: *Phlox carolina*×*Phlox maculata* 'Daughter of Pearl'.

Parentage:

*Female, or seed, parent.*—*Phlox carolina* 'Minnie Pearl', not patented.

*Male, or pollen, parent.*—*Phlox maculata* 'Alpha', not patented.

Propagation:

*Type.*—By stem cuttings.

*Time to initiate roots, summer.*—About three weeks at night temperatures about 15° C. and day temperatures about 26° C.

*Time to produce a rooted plant, summer.*—About six weeks at night temperatures about 15° C. and day temperatures about 26° C.

*Root description.*—Medium in thickness, fibrous; white in color.

*Rooting habit.*—Freely branching; medium density.

Plant description:

*Plant and growth habit.*—Herbaceous perennial; upright and mounding plant habit, columnar; vigorous growth habit; freely basal branching habit with about six to eight primary laterals developing per plant.

*Plant height.*—About 90 cm.

*Plant width (spread).*—About 60 cm.

*Lateral branches.*—Length: About 90 cm. Diameter: About 2.5 mm. Internode length: About 4.5 cm to 7.5 cm. Strength: Strong. Texture: Slightly pubescent. Color: Close to 145B, spotted and streaked with close to 59B.

Leaf description:

*Arrangement.*—Opposite, simple; sessile.

*Length.*—About 4 cm to 9.5 cm.

*Width.*—About 1.3 cm to 1.6 cm.

*Shape.*—Lanceolate.

*Apex.*—Acute.

*Base.*—Gradually tapering.

*Margin.*—Entire.

*Texture, upper and lower surfaces.*—Glabrous; thick; waxy.

*Venation pattern.*—Pinnate.

*Color.*—Developing and fully expanded leaves, upper surface: Close to 139B; venation, close to 139B. Developing and fully expanded leaves, lower surface: Close to 139C; venation, close to 139C.

Flower description:

*Flower form and flowering habit.*—Single rotate and salverform flowers arranged in terminal compound panicles; panicles conical in shape; freely flowering habit with about 70 to 80 flowers developing per inflorescence; flowers face upright to outwardly.

*Fragrance.*—Moderately fragrant; sweet.

*Natural flowering season.*—Early flowering habit, plants begin flowering about eight weeks after planting; plants flowering continuously from mid-spring to early summer in Pennsylvania.

*Postproduction longevity.*—Flowers last about seven to ten days on the plant and as a cut flower; flowers not persistent.

*Flower buds.*—Height: About 2.5 cm. Diameter: About 3.5 mm. Shape: Elongated oblong. Color: Close to 74C; distally, close to 155D.

*Inflorescence height.*—About 8 cm to 20 cm.

*Inflorescence diameter.*—About 8 cm to 10 cm.

*Flower diameter.*—About 2.1 cm to 2.3 cm.

*Flower depth.*—About 2.5 cm.

*Flower throat diameter.*—About 1.8 mm.

*Flower tube length.*—About 2.5 cm.

*Flower tube diameter, at base.*—About 1.5 mm.

*Petals*.—Quantity per flower and arrangement: Typically five in a single whorl; petals fused at the base into a narrow tube. Lobe length: About 1 cm to 1.1 cm. Lobe width: About 1.1 cm. Shape: Rhomboidal. Apex: Obtuse. Margin: Entire. Texture: Petal lobes, upper and lower surfaces: Smooth, glabrous. Throat: Smooth, glabrous. Tube: Smooth, glabrous. Color: Developing and fully expanded petal lobes, upper surface: Close to 155D shaded with close to 74C. Developing and fully expanded petal lobes, lower surface: Close to 155D; towards the base shaded with close to 74D. Flower throat: Close to 74D. Flower tube: Close to 74D.

*Sepals*.—Quantity per flower and arrangement: Typically five in a single whorl, fused towards the base into a slender tube. Length: About 8 mm. Width: About 2 mm. Shape: Lanceolate. Apex: Acute. Margin: Entire, membraneous. Texture, upper and lower surfaces: Smooth, glabrous. Color, upper surface: Close to 145B. Color, lower surface: Close to 145B shaded with close to 70B.

*Peduncles*.—Length: About 2 cm. Diameter: About 1 mm. Angle: Erect. Strength: Strong. Texture: Smooth, glabrous. Color: Close to 145B with irregular spotting and streaking, close to 59B.

*Pedicels*.—Length: About 4 mm to 5 mm. Diameter: About 0.5 mm. Angle: About 30° from peduncle axis. Strength: Strong. Texture: Pubescent. Color: Close to 145B.

*Reproductive organs*.—Stamens: Quantity per flower: Typically five. Filament length: About 1.5 mm. Anther shape: Oval. Anther length: About 2 mm. Anther color: Close to 17A. Pollen amount: Moderate. Pollen color: Close to 17A. Pistils: Quantity per flower: One. Pistil length: About 2.5 cm. Stigma shape: Tri-parted. Stigma color: Close to 154C. Style length: About 2.2 cm. Style color: Close to 154C. Ovary color: Close to 145B.

*Seeds*.—Quantity per flower: About one to three. Length: About 3 mm. Diameter: About 2 mm. Color: Close to 200C.

Disease & pest resistance: Plants of the new *Phlox* have been observed to be resistant to Powdery Mildew. Plants of the new *Phlox* have not been observed to be resistant to pests and other pathogens common to *Phlox* plants.

Garden performance: Plants of the new *Phlox* have been observed to have good garden performance and tolerate rain and wind and to temperatures ranging from about −30° C. to 45° C.

It is claimed:

1. A new and distinct *Phlox* plant named 'Daughter of Pearl' as illustrated and described.

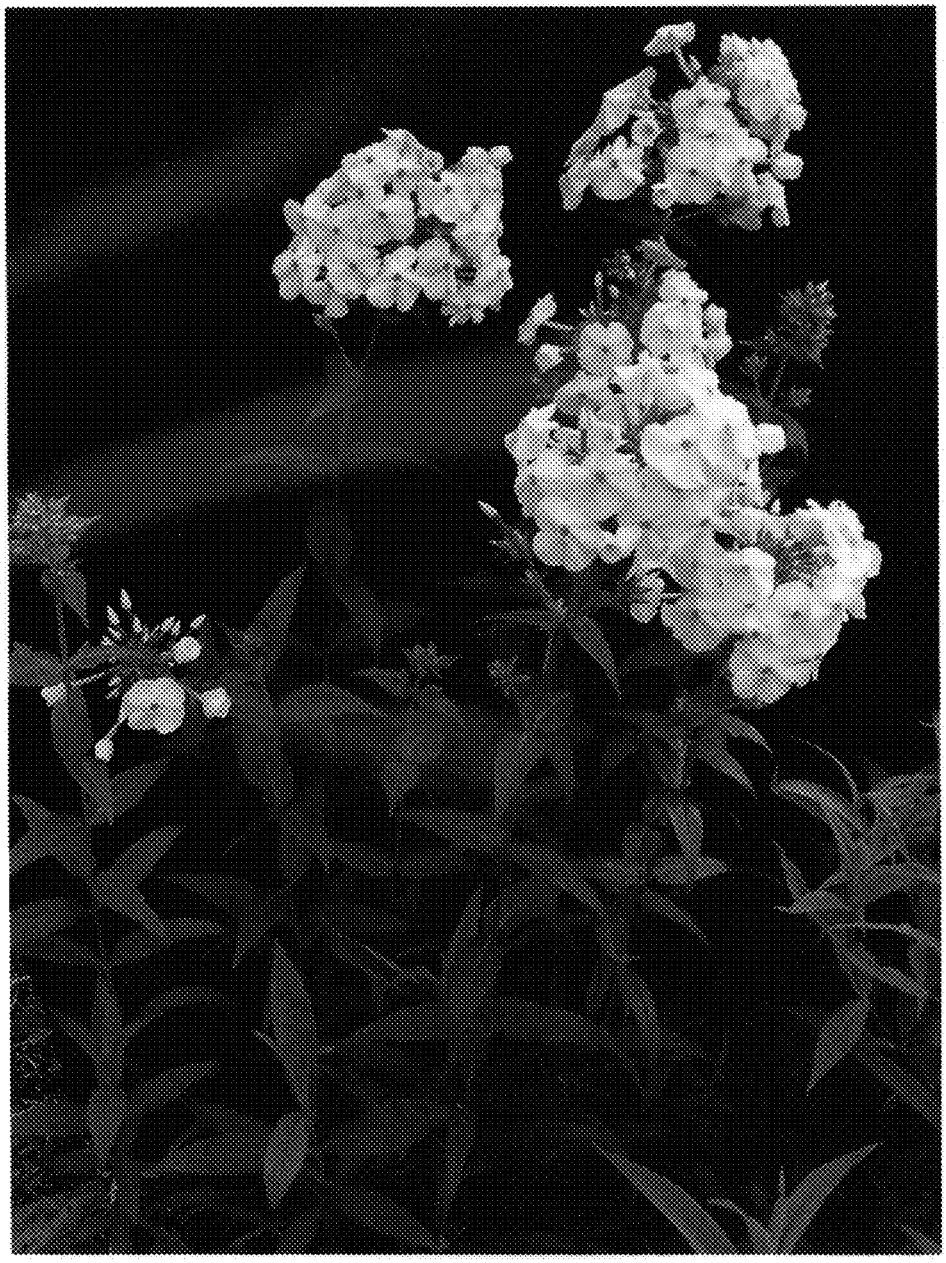

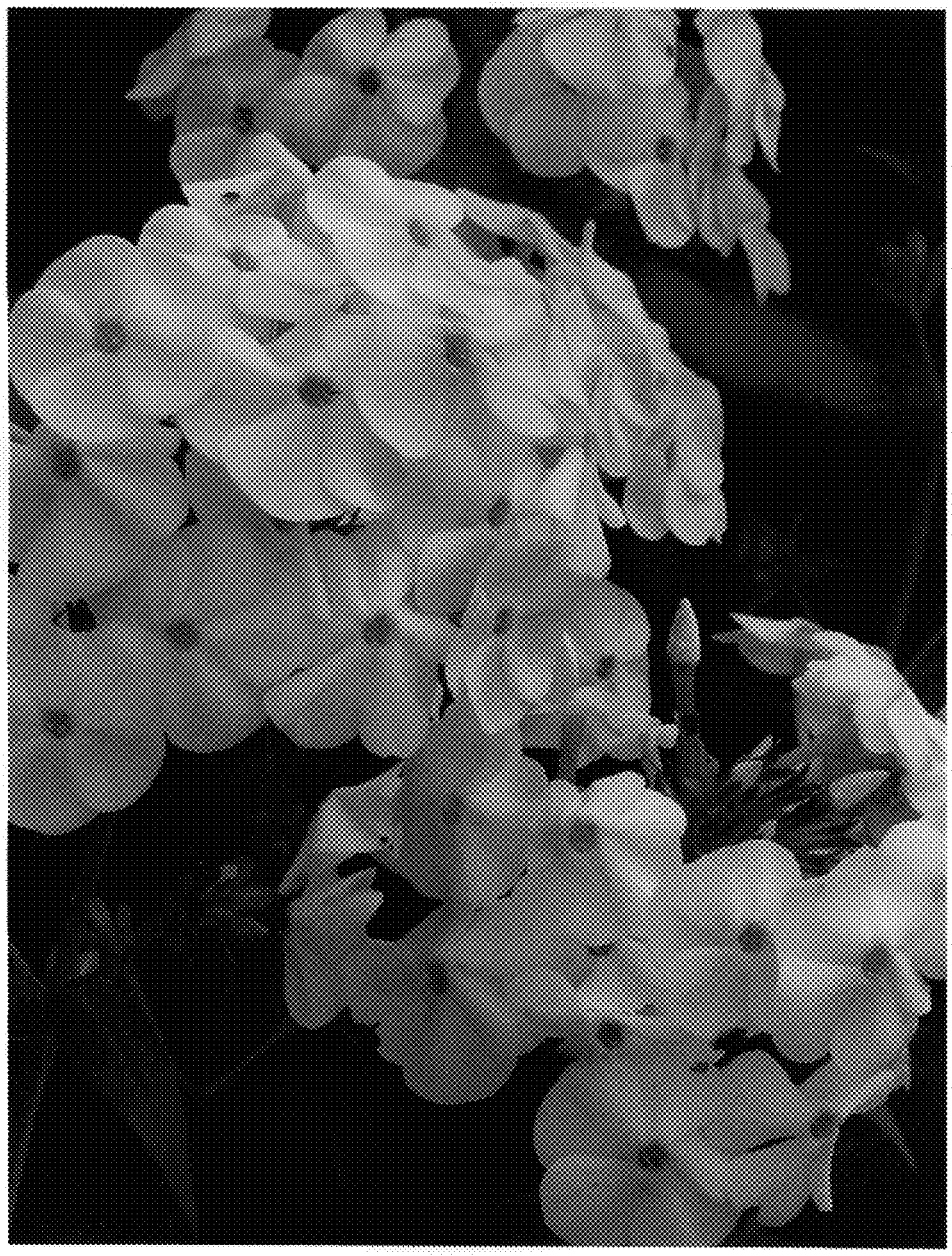

* * * * *